(12) United States Patent
Takimoto et al.

(10) Patent No.: US 9,629,604 B2
(45) Date of Patent: Apr. 25, 2017

(54) ULTRASONIC DIAGNOSTIC APPARATUS

(75) Inventors: Masao Takimoto, Otawara (JP);
Muneki Kataguchi, Nasushiobara (JP);
Fumiyasu Sakaguchi, Otawara (JP);
Akihiro Kakee, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 835 days.

(21) Appl. No.: 11/610,730

(22) Filed: Dec. 14, 2006

(65) Prior Publication Data

US 2007/0167766 A1    Jul. 19, 2007

(30) Foreign Application Priority Data

Dec. 26, 2005  (JP) .................................. 2005-373346

(51) Int. Cl.
  A61B 8/00    (2006.01)
  A61B 8/06    (2006.01)
  A61B 8/08    (2006.01)

(52) U.S. Cl.
  CPC ............... *A61B 8/06* (2013.01); *A61B 8/488* (2013.01)

(58) Field of Classification Search
  CPC ................................ A61B 8/06; A61B 8/488
  USPC ................................................. 600/437–456
  See application file for complete search history.

(56) References Cited

U.S. PATENT DOCUMENTS

| 5,375,599 | A  | * | 12/1994 | Shimizu ........................ 600/440 |
| 5,544,659 | A  | * | 8/1996  | Banjanin ....................... 600/455 |
| 6,099,471 | A  | * | 8/2000  | Torp et al. .................... 600/438 |
| 6,577,967 | B2 | * | 6/2003  | Mo et al. ........................ 702/76 |
| 6,869,401 | B2 | * | 3/2005  | Gilbert et al. ................. 600/459 |
| 2002/0019590 | A1 | * | 2/2002 | Bang et al. .................... 600/454 |
| 2003/0045797 | A1 | * | 3/2003 | Christopher et al. ......... 600/453 |
| 2004/0015079 | A1 | * | 1/2004 | Berger et al. ................. 600/437 |
| 2006/0079782 | A1 | * | 4/2006 | Beach et al. .................. 600/450 |
| 2007/0167793 | A1 | * | 7/2007 | Dala-Krishna et al. ...... 600/455 |
| 2007/0167794 | A1 | * | 7/2007 | Dala-Krishna ............... 600/455 |
| 2008/0234580 | A1 | * | 9/2008 | Bruce et al. .................. 600/441 |

FOREIGN PATENT DOCUMENTS

| JP | 8-308843 | 11/1996 |
| JP | 9-51896 | 2/1997 |
| WO | WO 03/019227 A1 | 3/2003 |

OTHER PUBLICATIONS

"Ultrasonic Technique for Imaging Tissue Vibrations: Preliminary Results" by Sikdar et al, Ultrasound in Medicine and Biology, vol. 31, No. 2, p. 221-232, Feb. 2005.*

(Continued)

*Primary Examiner* — Rajeev Siripurapu
(74) *Attorney, Agent, or Firm* — Oblon, McClelland, Maier & Neustadt, L.L.P.

(57) ABSTRACT

There is provides an ultrasonic diagnostic apparatus including a judgment unit which judges a folded back phenomenon of velocity based on signal information of a Doppler spectrum among signals received in a circulatory organ diagnostic region, a decision unit which decides whether the signals received are blood flow signals or tissue signals, and a change/adjustment unit which changes or adjusts at least one of a velocity range, a baseline position, a transmission/reception condition, a gain allocation, setting of a Wall Filter, a scrolling speed, and a range gate size.

2 Claims, 5 Drawing Sheets

(56) References Cited

OTHER PUBLICATIONS

"Tissue Doppler echocardiographic evidence of atrial mechanical dysfunction in coronary artery disease" by Yu et al, International Journal of Cardiology, 105, (Mar. 2005), p. 178-185.*
Dickey, R.P., "Doppler ultrasound investigation of uterine and ovarian blood flow in infertility and early pregnancy", Human Reproduction Update 1997, vol. 3, No. 5, pp. 467-503.*
U.S. Appl. No. 12/017,868, filed Jan. 22, 2008, Osumi, et al.
Japanese Office Action mailed on May 10, 2011 for JP 2005-373346 filed Dec. 26, 2005 with English translation.

* cited by examiner

ULTRASONIC DIAGNOSTIC APPARATUS

CROSS-REFERENCE TO RELATED APPLICATION

This application is based upon and claims the benefit of priority from prior Japanese Patent Application No. 2005-373346, filed Dec. 26, 2005, the entire contents of which are incorporated herein by reference.

BACKGROUND OF THE INVENTION

1. Field of the Invention

The present invention relates to an ultrasonic diagnostic apparatus, and particularly to an ultrasonic diagnostic apparatus which utilizes Doppler effect of ultrasonic wave to diagnose kineticism of moving bodies in side the body such as blood and kineticism of tissues.

2. Description of the Background Art

Figure 1:
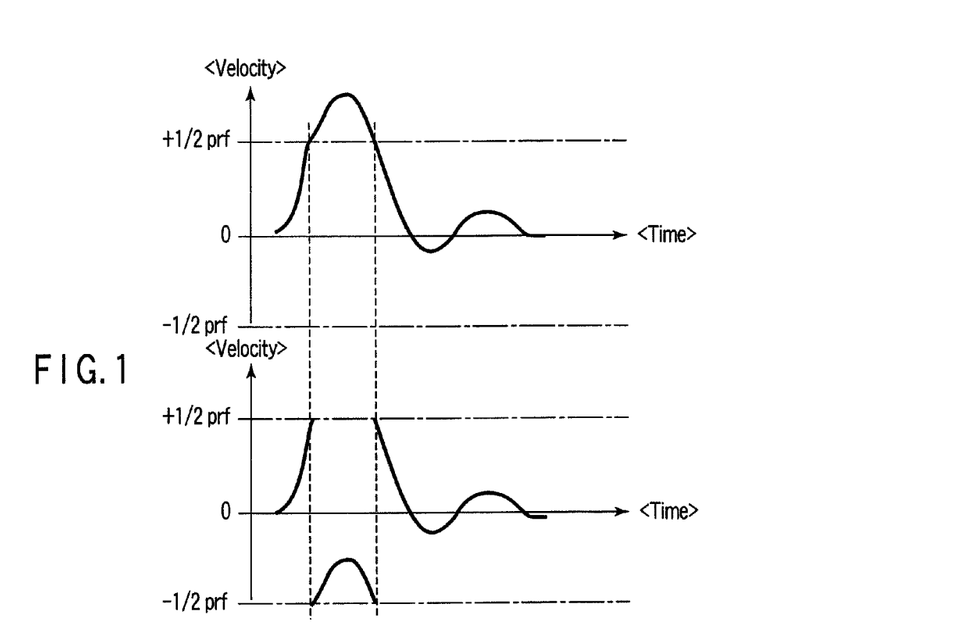
FIG. 1 is a view indicating a condition in which waveforms are folded back.
Figure 2A:
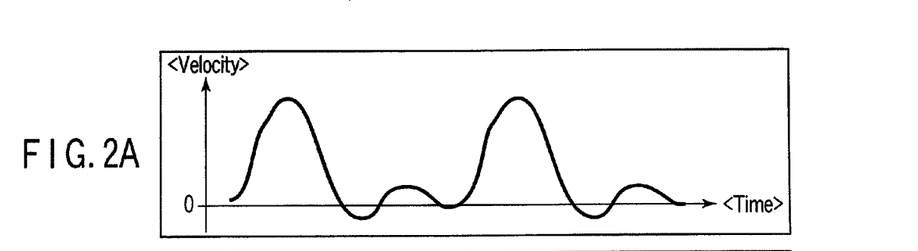
FIGS. 2A to 2C are views indicating a method of which the folded back waveform or the like is adjusted into an adequate waveform.
Figure 2B:
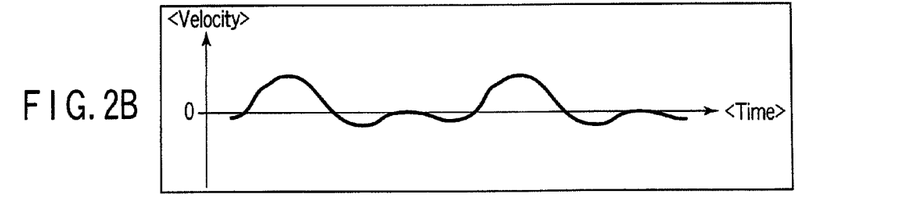
Figure 2C:
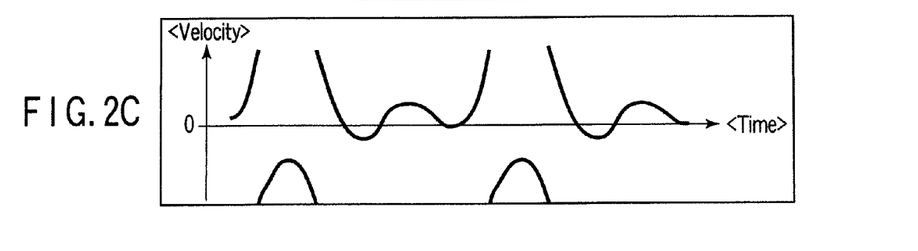

In circulatory organ routine checkup examinations, decisions of abnormal systolic/diastolic function or decisions of abnormal valve disorders in a heart are performed by utilizing blood flow signals, and further evaluations of systolic/diastolic function in left ventricular cardiac muscle or abnormal local wall movements are performed by utilizing wall (tissue) signals. In general, the diagnosis is carried out by switching between a blood flow analysis mode (PWD mode) for evaluating only blood flow and a tissue analysis mode (TDI-PW mode) for evaluating only the wall (tissue) signals in case of effecting the former and the latter decisions. In this case, when the frequency detected exceeds the repetition frequency (±½ PRF), the waveform which is folded back is obtained as shown in FIG. 1. As described above, it is necessary for an examiner to properly set a pulse repetition frequency (rate frequency) or a baseline position in response to a blood velocity (tissue velocity) in order to cause a waveform which has small amplitudes as shown in FIG. 2B or which is folded back as shown in FIG. 2C to be the waveform as shown in FIG. 2A. For this reason, the adjustment required takes a much operation time, and further it is a remarkable burden on the examiner.

In this respect, recently in a Doppler mode, there has been disclosed a technology for automatically adjusting the velocity range and the baseline position on an apparatus side in order that blood flow signals and tissue signals having various velocities and directions are displayed so as to facilitate visualization always without being folded back (see Jpn. Pat. Appln. KOKAI Publication No. 8-308843). In the technology, a signal existence region is detected with regard to a range in which detectable frequencies exist, whereby the repetition frequency and the baseline position are automatically set. As a result, the burden on an examiner can be reduced, whereby a time required for diagnosis can be remarkably shortened. Although there are a variety of algorithms with respect to the automatic adjustment, when the function therefor is utilized, complications in the operations during the routine examination can be remarkably improved, whereby the examination efficiency is improved. In the automatic adjustment method, when a user pushes once the button provided on the panel of an apparatus, it is usually possible to obtain the Doppler waveform adjusted automatically.

However, the existing Doppler automatic adjustment function is a mere function for analyzing the signals received to adjust the velocity range (repetition frequency), the baseline position and the like in order to exclude a folded back phenomenon of the Doppler signals received. Accordingly, the existing Doppler automatic adjustment function does not include a function for changing the transmission/reception condition for obtaining a further optimum reception signal with respect to the received signals.

Moreover, the existing Doppler automatic adjustment function does not include even a function for deciding whether the received signal is a blood flow signal or a tissue signal. Accordingly, there is neither a function for providing a method for transmitting/receiving the optimum blood flow signal together with the existing automatic adjustment function when the signal received is decided to be a blood flow signal, nor a function for providing a method for transmitting/receiving the optimum tissue signal together with the existing automatic adjustment function when the signal received is decided to be a tissue signal.

BRIEF SUMMARY OF THE INVENTION

The present invention provides an ultrasonic diagnostic apparatus capable of displaying an appropriate waveform without particular regard to analysis modes of a blood flow signal and a tissue signal in the case where the blood flow signal analysis and the tissue signal analysis are performed.

In the present invention, the parameter change to observe a better image is performed in addition to the adjustments of a velocity range and a baseline position, when the waveform display is not suitable as in the case of the appearance of folded back received signals.

An ultrasonic diagnostic apparatus according to one aspect of the present invention comprises: a judgment unit which judges a folded back phenomenon of velocity based on signal information of a Doppler spectrum among signals received in a circulatory organ diagnostic region; a decision unit which decides whether the signals received are blood flow signals or tissue signals; and a change/adjustment unit which changes or adjusts at least one of a velocity range, a baseline position, a transmission/reception condition, a gain allocation, setting of a Wall Filter, a scrolling speed, and a range gate size.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 4A to 4C are a flowchart and diagrams, wherein

DETAILED DESCRIPTION OF THE INVENTION

Figure 3:
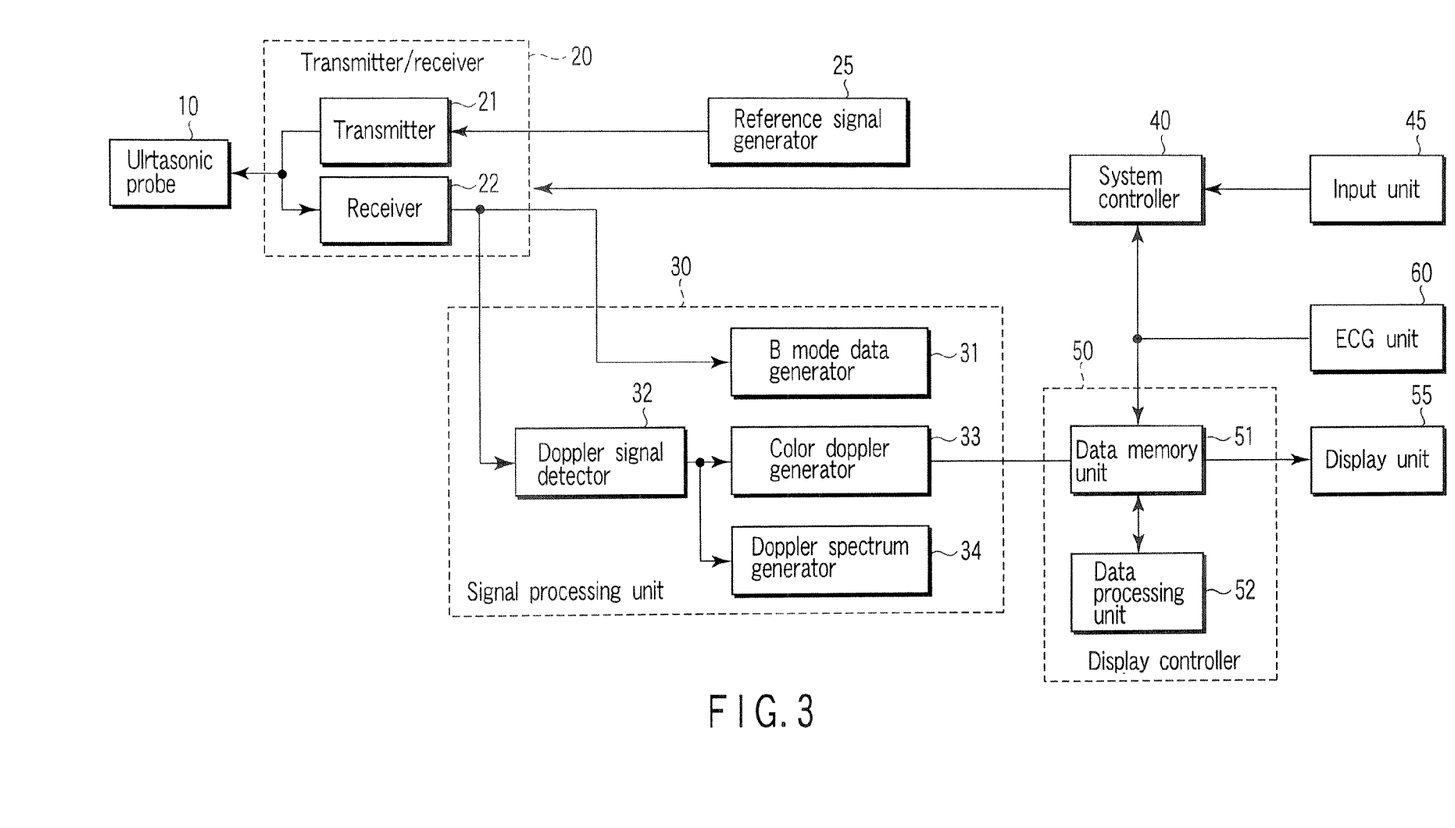
FIG. 3 is a block diagram showing a schematic configuration of an ultrasonic diagnostic apparatus according to an embodiment of the present invention.

An embodiment of the present invention will be described referring to the accompanying drawings. FIG. 3 is a block diagram showing a schematic configuration of an ultrasonic diagnostic apparatus according to an embodiment of the present invention.

In FIG. 3, the ultrasonic diagnostic apparatus according to the present embodiment comprises an ultrasonic probe 10, a transmitter/receiver 20, a signal processing unit 30, a system controller 40, a display controller 50, and an ECG (Electrocardiogram) unit 60. The ultrasonic probe 10 comprises a plurality of ultrasonic transducers and functioning to transmit/receive ultrasonic waves with respect to a body to be diagnosed (not shown). The transmitter/receiver 20 controls the ultrasonic transducers. The signal processing unit 30 performs the signal processing for the ultrasonic waves received. The system controller 40 controls the whole system. The display controller 50 performs the display control with respect to a display unit 55. An input unit 45 corresponds, for example, to an automatic adjustment function switch disposed on a panel (not shown) in the present embodiment.

The transmitter/receiver 20 includes a transmitter 21, and a receiver 22. A reference signal is input to the transmitter 21 from a reference signal generator 25 to output a driving signal to the ultrasonic transducers of the ultrasonic probe 10. The receiver 22 inputs a reception signal from the ultrasonic probe 10. The signal in which a reception treatment is performed in the receiver 22 is input to the signal processing unit 30, and the signal processing unit 30 performs a prescribed treatment. The signal from the signal processing unit 30 is input to a B mode data generator 31 and a Doppler signal detector 32. The B mode data generator 31 generates B mode data based on the signal input. The Doppler signal detector 32 detects Doppler signals among the reception signals output from the receiver 22. The Doppler signals are output to a color Doppler generator 33 for generating color Doppler data, and a Doppler spectrum generator 34 for generating Doppler spectra. Thus, the B mode data, the color Doppler data, and the Doppler spectra are output from the signal processing unit 30 to the display controller 50.

The display controller 50 comprises a data storing unit 51, and a data processing unit 52. The data storing unit 51 temporarily stores the respective data output from the signal processing unit 30. The respective data stored temporarily in the storing unit 51 is subjected to a variety of processings such as image processing, and superposition processing in the data processing unit 52. The respective data stored temporarily in the data storing unit 51 is converted further into the data for display use, and then it is output to the display unit 55.

Figure 4A:
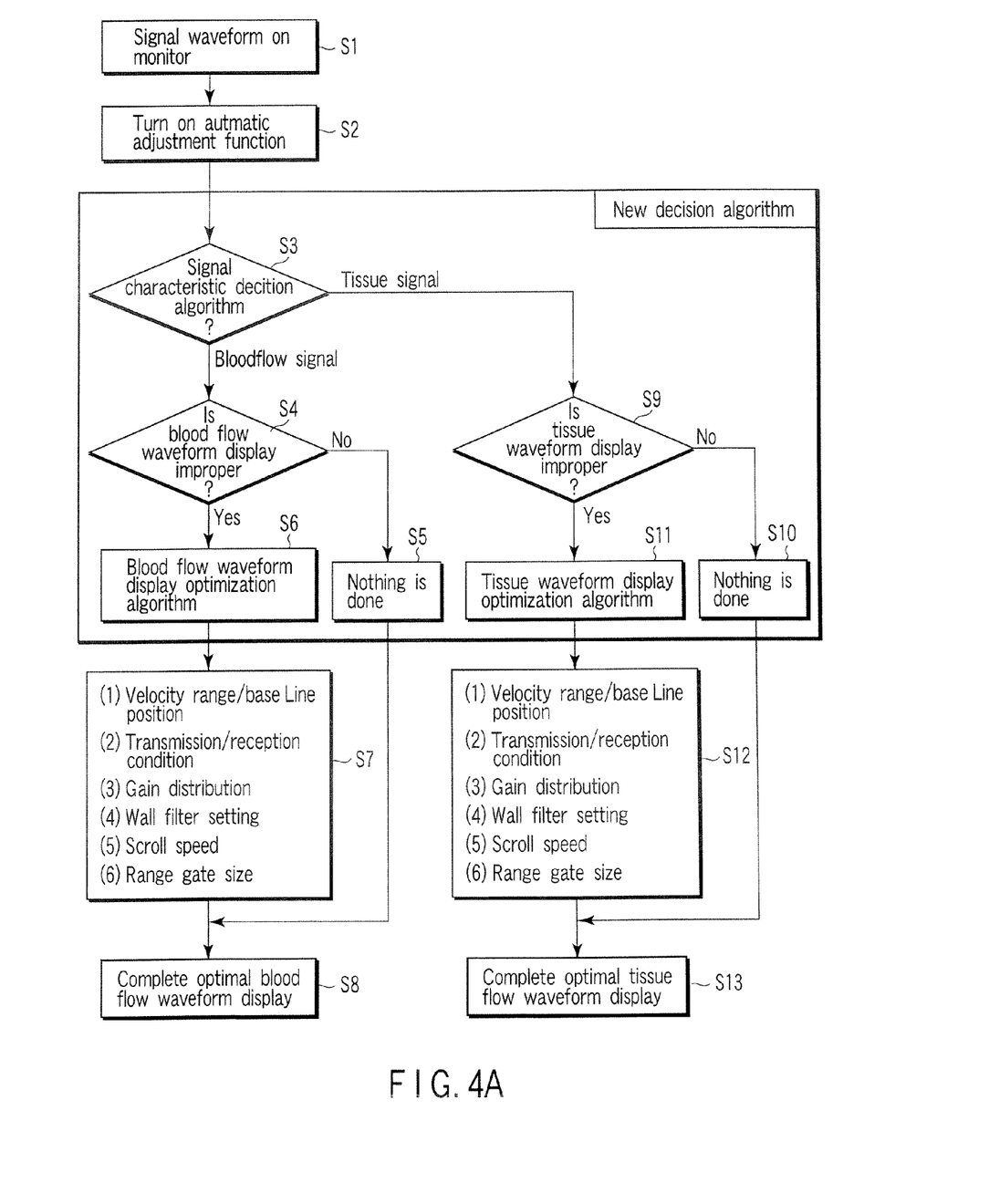
FIG. 4A is a flowchart showing a flow of operations of the ultrasonic diagnostic apparatus according to one embodiment of the present invention as well as FIGS. 4B and 4C are diagrams each showing a display of the optimum waveform.
Figure 4B:
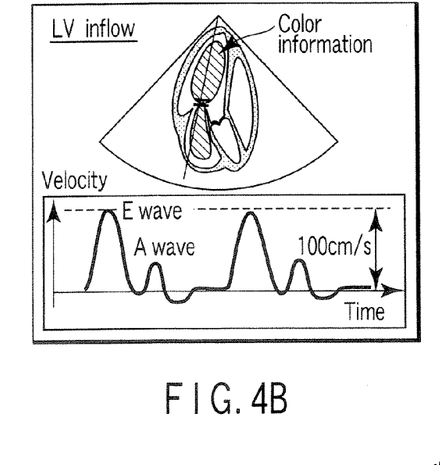
Figure 4C:
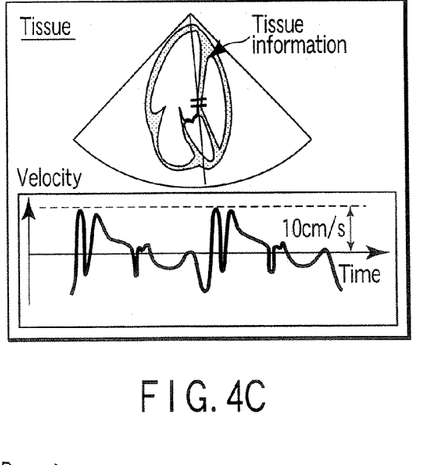

With reference to FIGS. 4A to 4C, operations of the ultrasonic diagnostic apparatus according to the embodiment of the present invention having the configuration as described above will be described. FIG. 4A is a flowchart showing a flow of the operations in the ultrasonic diagnostic apparatus according to the embodiment of the invention, and FIGS. 4B and 4C are diagrams each showing a display of the optimum waveform. It is to be noted herein that since all the control for the operations indicated in FIG. 4A is carried out by the system controller 40, unless otherwise particularly mentioned, it should be considered that the control in question is made by the system controller 40.

First, an examiner recognizes a Doppler waveform on the basis of the signal waveform on a monitor (step S1). Then, when the examiner decides the requirement for adjusting the velocity range and the position of baseline, the examiner turns "ON" the automatic adjustment function switch provided on the panel and the like on the apparatus (step S2). In this case, the automatic adjustment function switch may be provided on the other place than the panel. Furthermore, it may be arranged in such that the same behavior as in the case where the above-described automatic adjustment function switch is turned "ON" may be carried out, when the system controller 40 decides the requirement for adjusting the velocity range and the position of baseline, without providing the automatic adjustment function switch.

Figure 5:
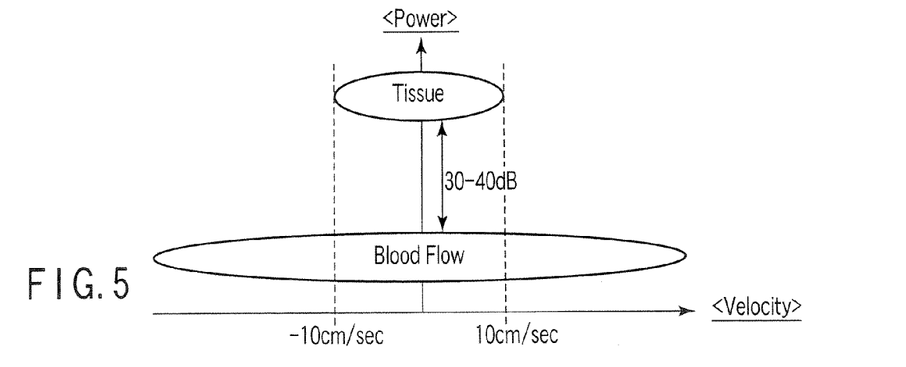
FIG. 5 is a diagram showing a relative relationship between the blood flow signals and the tissue signals.
Figure 6:
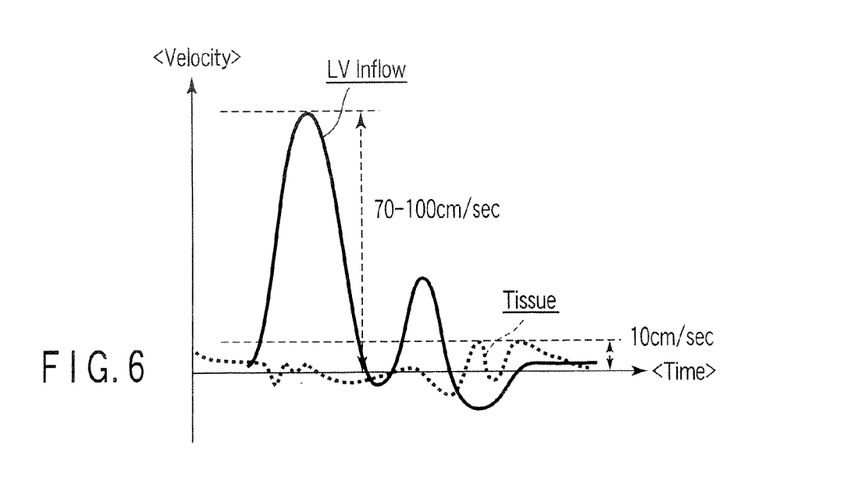
FIG. 6 is a diagram showing a relative relationship between the left ventricular inflow blood flow signals and the tissue signal flow signals.

When the automatic adjustment function switch is turned "ON", it is decided whether the signal received is a tissue signal or a blood flow signal in a characteristic decision algorithm among first decision algorithms (step S3). Referring to FIGS. 5 and 6, the decision algorithms will be described. FIG. 5 is a diagram showing a relative relationship between blood flow signals and tissue signals, while FIG. 6 is a diagram showing a relative relationship between left ventricular inflow blood flow signals and tissue signal flow signals. From the graphical representation in FIG. 5 of signal intensity characteristics of the blood flow signals and tissue signals, it is found that the signal intensity of blood flow signal is weaker than that of tissue signal by usually around 30 to 40 dB, and that the frequency characteristics (velocity characteristics) are distributed extensively. On one hand, it is found, from the graphical representation of the frequency characteristics (velocity characteristics) in FIG. 6, that the frequency characteristics of tissue signal are very low (the velocity is slow), and more specifically, the movement of a tissue which is usually considered in echocardiography is around 10 cm/second, while a blood velocity is around 70 to 100 cm/second. By utilizing these characteristics, it is possible to simply decide whether the signal now being received is a blood flow signal or a tissue signal by setting, for example, a threshold value. As a result of the arrangement, it becomes possible to decide automatically whether the signal received is a blood flow signal or a tissue signal.

In step S3, when it is decided that the received signal is a blood flow signal, it is further decided whether or not the blood flow signal is in a folded back phenomenon, and whether or not the blood flow signal is properly displayed in the display region (step S4). In the decision, when the blood flow signal is properly displayed ("No" in step S4), the completed waveform is displayed as it is without changing the repetition frequency and the baseline position (step S5 and step S8). In this case, even if the waveform display is proper, the transmission/reception condition may be changed in the case where the range gate is in a depth position at which the signal can be more sensitively received. In general, if there is no problem in the frequency band of a probe, a neat waveform is obtained in good sensitivity in such a manner that the transmission/reception is repeated as a result of transition from the frequency transmitted/received at present to a lower frequency while taking the attenuation characteristics of ultrasonic wave in living body into consideration.

In step S4, when it is decided that the blood flow signal waveform is improper ("Yes" in step S4), a blood flow waveform display optimization algorithm is started (step S6) to change/adjust at least one item in the following items (step S7). In changing the under-mentioned parameters, either all the parameters may be changed at the same time, or a changeable parameter may be selectively determined in accordance with an examiner's intention.

(1) An adjustment of velocity range or a baseline position.
(2) A change in a transmission/reception condition for receiving a signal with good sensitivity for the position of a range gate.
(3) The optimization of gain allocation for avoiding saturation as a result of deciding presence or absence of a saturation phenomenon in the signal circuit.
(4) A change in setting a Wall Filter according to the change of a velocity range.
(5) A change in a scrolling speed in which a properly round figured number of heart beat, for example, two heart beats or three heart beats can be displayed in the display region according to a Doppler waveform display method.
(6) A fine adjustment of a range gate width due to the characteristics of the signal received.

Thus, the optimum blood flow waveform as shown in FIG. 4B is displayed (step S8).

Next, when it is decided in step S3 that the signal is a tissue signal by a decision algorithm of signal characteristics ("tissue signal" in step S3), it is further decided whether or not the tissue signal is in a folded back phenomenon, and whether or not the tissue signal is properly displayed in the display region (step S9). In the decision, when the tissue signal is properly displayed, the completed waveform is displayed as it is without changing the repetition frequency and the baseline position (step S10 and step S13). In this case, even if the waveform display is selectively proper, a gain allocation for avoiding saturation may be applied again as a result of deciding presence or absence of a saturation phenomenon in the signal circuit. In the setting, it may be arranged previously to be selectable which factor should be adjusted in accordance with the examiner's intention.

In step S9, when it is decided that the tissue signal waveform is improper ("Yes" in step S9), a tissue waveform display optimization algorithm is started (step S11) to change/adjust at least one parameter in the changeable parameters as in the case of step S7 (step S12). In this case, a transmission/reception condition may be changed in order to obtain a sharp and neat tissue signal waveform at the same time of adjusting properly a velocity range and a baseline position. In general, since the reception signal from a tissue shows sufficient sensitivity, it is better to select a higher frequency, which can more narrows the beam. Since a tissue signal has usually a velocity of around 10 cm/second, it is suitable to set the Wall Filter for removing a clutter signal which forms an obstacle to watch a blood flow signal at a comparatively low level. Moreover, since it is desired to clearly display both the signals during diastole and systole in case of observing tissue signals, a scrolling speed is usually set at a higher level than that of observing a blood flow. At the same time, it is preferred to set usually a broader range gate width than that in case of evaluating a blood flow. As a result, the optimum tissue waveform is displayed as shown in FIG. 4C (step S13).

Figure 7:
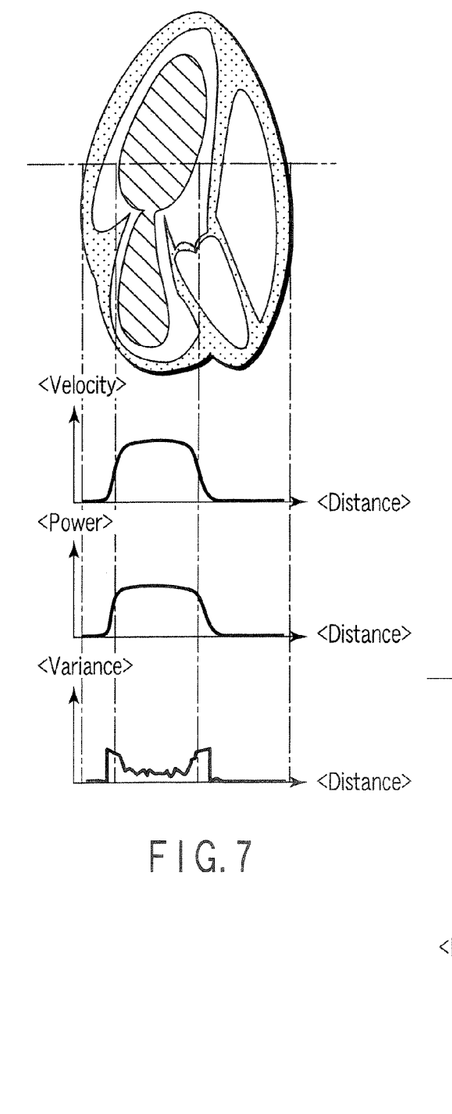
FIG. 7 is a characteristic diagram showing parameter examples used in the case where color information is analyzed.
Figure 8:
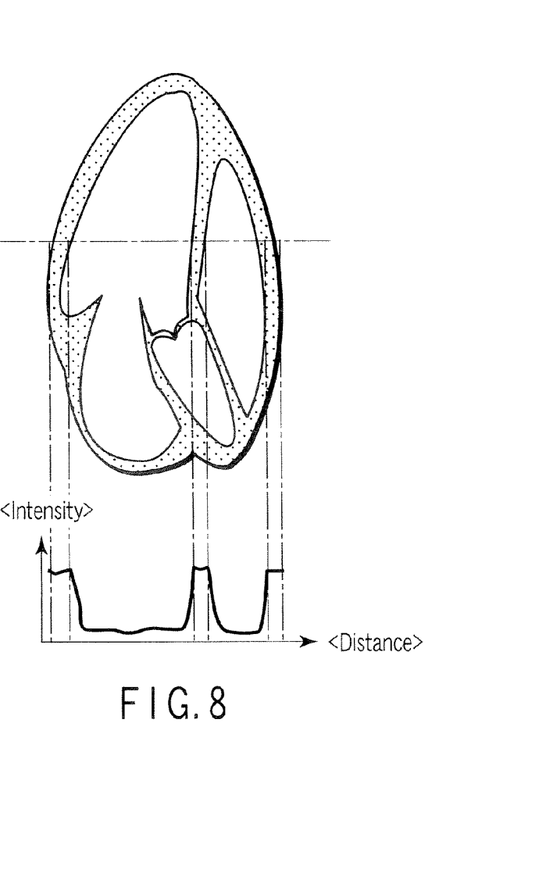
FIG. 8 is a characteristic diagram showing parameter examples used in the case where B information is analyzed

Conventionally, when a blood flow signal is diagnosed, a blood flow analysis mode is selected as described above; and either a variety of setting operations are adjusted manually or adjusted automatically. In case of diagnosis of a tissue signal, it is required to select a tissue signal analysis mode. On the other hand, it is possible to provide an examiner with the optimum diagnostic image without regard to these two modes in the present embodiment. Although the decision for signal whether it is a blood flow signal or a tissue signal may be performed by using only characteristics of Doppler signal waveform by analyzing at least one of velocity, signal intensity, and duration, the decision for signal may be made by using the color information and B information in addition to the characteristics of Doppler signal waveform. FIG. 7 is a characteristic diagram of parameter examples used in case of analyzing color information, while FIG. 8 is a characteristic diagram of a parameter example used in case of analyzing B information. In FIG. 7, it is possible to utilize velocity information, Power information, and distribution information, while in FIG. 8, it is possible to utilize luminance information (intensity).

As shown in FIGS. 7 and 8, when a Doppler signal is acquired, a range gate is set in addition to the display by a B mode or a color mode, so that it is found that the range gate set is provided on the tissue or in the heart chamber, i.e. a position where the so-called blood flow signals shall be present.

As described above, according to the present invention, it becomes possible to provide always the optimum transmission/reception condition, velocity range, and zero shift position at once by utilizing usually characteristics of blood flow and core wall movement without applying mode transition to each of the signals of blood flow and core wall being quite different from one another. As a result, the work flow in circulatory organ routine checkup examinations is made to be simple, resulting in improvements in the checkup examination efficiency. In the present invention, as described above, when signal characteristics of blood flow and tissue are used, a Doppler spectrum having no folded back is provided without switching particularly intentionally between a blood flow analysis mode and a tissue analysis mode, and further the Doppler spectrum which is easily observed by an examiner is automatically provided at once. Thus, a burden is reduced with respect to the examiner, whereby a term for the diagnosis may be shortened. Besides, the work flow in circulatory organ routine checkup examinations may also be made simple, and it results in improvements in the examination efficiency.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An ultrasonic diagnostic apparatus, comprising: a system controller configured to judge whether signals received in a circulatory organ diagnostic region are blood flow signals or tissue signals by analyzing B-mode luminance information at a range gate position; and a display configured to display a waveform regarding the blood flow signals or a waveform regarding the tissue signals, wherein the system controller is further configured to, when the received signals are judged to be the blood flow signals, scroll the waveform regarding the blood flow signals at a predetermined first speed on the display, and when the received signals are judged to be the tissue signals, scroll the waveform regarding the tissue signals at a predetermined second speed on the display, the second speed being faster than the first speed, to display the tissue signals during diastole and systole.

2. An ultrasonic diagnostic apparatus, comprising: a system controller configured to judge whether signals received in a circulatory organ diagnostic region are blood flow signals or tissue signals by analyzing color information at least one of power and velocity of the received signals at a range gate position; and a display configured to display a waveform regarding the blood flow signals or a waveform regarding the tissue signals, wherein the system controller is further configured to, when the received signals are judged to be the blood flow signals, scroll the waveform regarding the blood flow signals at a predetermined first speed on the display, and when the received signals are judged to be the tissue signals, scroll the waveform regarding the tissue signals at a predetermined second speed on the display, the second speed being faster than the first speed, to display the tissue signals during diastole and systole.

* * * * *